United States Patent [19]
Globe

[11] Patent Number: 5,118,292
[45] Date of Patent: Jun. 2, 1992

[54] STRESS BREAKER APPLIANCE SOCKET

[76] Inventor: Harold Globe, 200 S. Carson Rd., Beverly Hills, Calif. 90211

[21] Appl. No.: 705,075

[22] Filed: May 24, 1991

[51] Int. Cl.⁵ .............................................. A61C 13/28
[52] U.S. Cl. .................................................... 433/170
[58] Field of Search ................ 433/170, 181, 182, 183

[56] References Cited

U.S. PATENT DOCUMENTS

| | | | |
|---|---|---|---|
| 1,665,975 | 4/1928 | Oscher | 433/170 |
| 3,388,471 | 6/1968 | Thompson | 433/170 |
| 3,999,297 | 12/1976 | Globe | 433/170 |

Primary Examiner—John J. Wilson

[57] ABSTRACT

The present invention is an improved female joint portion (40) for the Stress Breaker Appliance ® (10). It comprises a wedge shaped female socket (40) which will receive the wedge shaped male member (16) of the Stress Breaker Appliance ® (10). The female member (40) has two side walls (42) and a rear wall (44), and has an occlusal opening (50) and a gingival opening (52). It tapers inwardly in a gingival direction. As a result of the taper, the occlusal opening (50) is larger than the gingival opening (52) so that said male member (16) cannot fall below the gingival opening (52) of the female member (40). The two opposing walls (42) have holes (46) through them for retaining a connecting pin (36). The purpose of the pin (36) is to retain the wedge shaped male member (16) within the wedge shaped female member (40) and constrain their movements relative to each other. A flap (48) is pierced in the rear wall (44). The presence of this flap (48) ensures that the female member (40) will be securely retained in a false tooth (58) and the dental plastic (60) of the completed Stress Breaker Appliance ® (10).

5 Claims, 2 Drawing Sheets

STRESS BREAKER APPLIANCE SOCKET

BACKGROUND OF THE INVENTION

The present invention relates to the field of dental prostheses and more particularly to dental appliances incorporating a joint for avoiding application of stress to abutment teeth during mastication.

When a patient loses only some of his teeth, it is common practice to provide a removable appliance which will support false teeth for co-operation with the remaining teeth so that the patient can chew normally. Such appliances are retained in the correct position in the mouth by retainers which encircle the abutment teeth. There are several types of retainers: clasps, which encircle the tooth; semi-precision attachments, which partially encircle the tooth; and precision attachments, which are all internal and do not encircle the tooth. If these appliances are rigidly constructed, stresses induced by chewing are transmitted to the abutment teeth. The Stress Breaker Appliance ®, U.S. Pat. No. 3,999,297, solved the problem of transmitting stress to the abutment teeth by separating the appliance into at least two segments and then joining the segments with a special wedge shaped joint which allows small, guided motion of the portions relative to each other. The features of U.S. Pat. No. 3,999,297 are easily incorporated into a dental appliance by means of the investment casting or lost wax process. In fact molding kits for this purpose have been available for many years.

While the invention of U.S. Pat. No. 3,999,297 provided a great advance in the field of dental prostheses and provision of the molding kits made the dental technician's life easier, it was found by the inventor that a number of features of the original Stress Breaker Appliance ® could be improved. First, the female portion of the joint is joined to the frame of the rear portion of the appliance. Thus when repairs are needed, it is necessary to remanufacture the rear frame or at least perform major reconstruction. Second, since the female portion is so small and its faces so occluded, less skilled technicians have difficulty in making defect free castings. Third, once defects are introduced, they are difficult to remove.

If an improved female portion were to be developed which could be manufactured by less painstaking and less costly methods, and which could be incorporated into the dental plastic rather than into the frame, this would represent a great improvement in the Stress Breaker Appliance ® and satisfy a long felt need of dental technician. Also, an improved female portion would enable less expensive manufacture of dental appliances.

SUMMARY OF THE INVENTION

The present invention is an improved female joint portion for the Stress Breaker Appliance ®. It comprises a wedge shaped female member or socket which will receive the wedge shaped male member of the Stress Breaker Appliance ®. The female member has three walls, and is open at the top and bottom, i.e. it has gingival and occlusal openings. It tapers inwardly in a gingival direction. As a result of the taper, the occlusal opening is larger than the gingival opening so that the male member cannot pass below the bottom or gingival opening of the female member. The two opposing walls have holes through them for retaining a connecting pin. The purpose of the pin is to retain the wedge shaped male member of the Appliance within the wedge shaped female member and constrain their movements relative to each other. A flap is pierced in the rear wall. The presence of this flap ensures that the female member will be securely retained in a false tooth and the dental plastic of the completed Stress Breaker Appliance ®.

The improved female socket can be utilized in upper or lower dental prostheses. This improved female joint portion can be made by relatively inexpensive sheet metal fabrication techniques thus eliminating the necessity of investment casting. It does not have to be made a part of the rear frame of the Appliance; instead, it can be molded into the dental plastic of the completed appliance. With this configuration, it is much easier to rework or repair the Stress Breaker Appliance ®.

DETAILED DESCRIPTION OF THE PREFERRED EMBODIMENT

Figure 1:
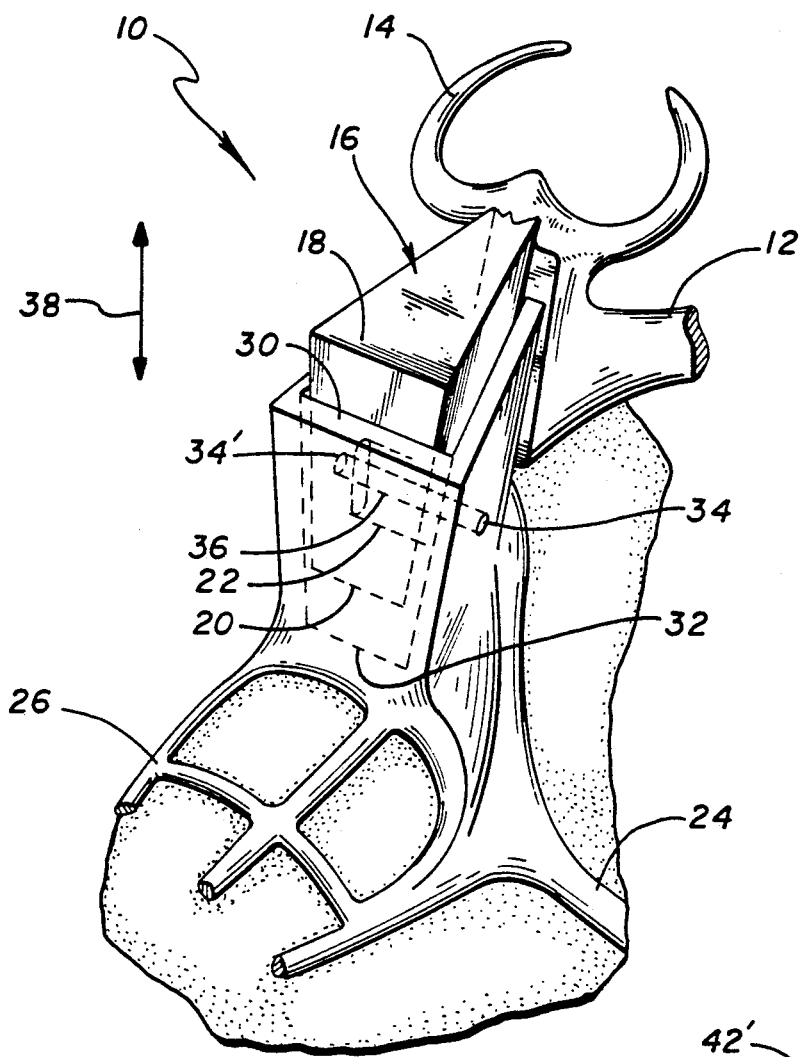
FIG. 1 is a fragmentary perspective view of a typical Appliance in accordance with U.S. Pat. No. 3,999,297.

FIG. 1 shows a partial perspective view of one embodiment of the original Stress Breaker Appliance ® 10 in accordance with U.S. Pat. No. 3,999,297. The main or front portion 12 has an encircling retainer 14 which encircles an abutment tooth (not shown). Affixed to this front portion 12 is a solid wedge 16. This wedge 16 tapers so that its top 18 is larger than its bottom 20. The wedge 16 is oriented so that its top 18 abuts the occlusal surfaces of the Appliance 10 while its bottom 20 is close to the gingival area of the Appliance 10. An elongated slot 22 traverses the wedge 16 in a direction transverse to the patient's remaining teeth.

The rear portion 24 has a frame 26 where the false teeth (not shown) will eventually be secured with dental plastic. At the forward end of the frame 26 is a wedge shaped socket or female member 28, which is shaped to receive the wedge 16. The female member 28 is also tapered so that its top 30 is larger than its bottom 32. Again the top 30 abuts the occlusal surfaces of the Appliance 10 while the bottom 32 is close to the gingival areas. Through the side walls of the female member 28 there are holes 34, 34', which correspond approximately with the slot 22.

The wedge 16 is retained within the confines of the female member by means of a pin 36 which traverses the slot 22 and is retained in the holes 34. The wedge 16 and female member 28 are able to move in relation to each other in the direction shown by the arrow 38. Travel in one direction is prevented by the tapers of the respective portions of the joint. Travel in the other direction is constrained by the travel of the pin 36 within the slot 22. Allowing small constrained motions of the wedge and female member in relation to each other allows small, controlled movements of the front 12 and rear 24 portions of the Appliance 10 in relation to each other. This motion relieves the stresses, induced by chewing, on the abutment teeth. Advantages and other variations of the original Stress Breaker Appliance ® 10 will be appreciated by reviewing U.S. Pat. No. 3,999,297.

The metal support of the forward 12 and rear 24 portions of the original Stress Breaker Appliance ® 10 are made by investment casting. Kits containing precision plastic replicas of the male wedge 16 and the female socket 28 have been available for many years. These plastic replicas are used by dental technicians to make wax models from which the frames 12, 24 are cast. More recently, metal female sockets 28 have been available. These are still made by investment casting but may be cemented into a modified false tooth. The sprue remaining on the investment cast socket 28 is used for locating and retention.

Figure 2:
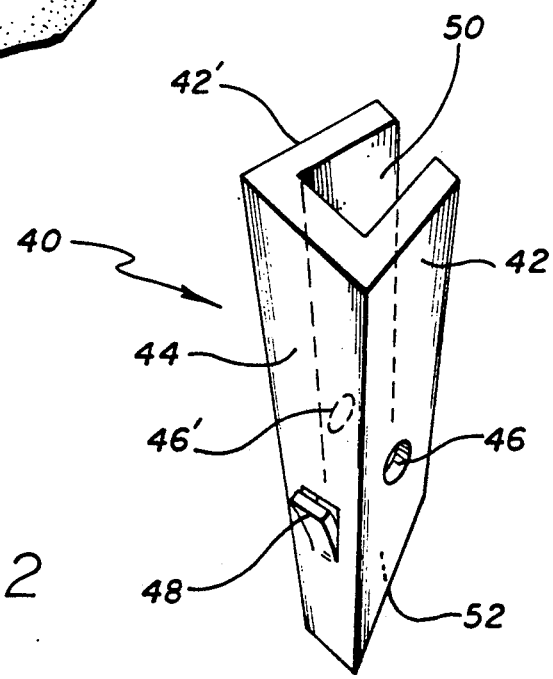
FIG. 2 is a perspective view of the improved female joint portion of this invention.

FIG. 2 is a perspective view of the improved female socket 40. As can be seen, the improved socket 40 is wedge shaped, and has two side walls 42, 42' and a rear wall 44. The improved female member 40 is open at the top and bottom and is also tapered so that its occlusal opening 50 is larger than its gingival opening 52. In each side wall, there is a hole 46, for alignment with the elongated slot 22 in the male wedge 16. A flap 48 is cut into the rear wall 44. A rectangular flap pointing upwards is illustrated. However, the flap could just as easily be triangular or semicircular or any other convenient shape, and could point down or in any other convenient direction.

The improved female socket 40 is not made by investment casting. Instead it is made from sheet metal by standard metal forming techniques such as blanking, piercing and stamping. In the preferred embodiment the improved female socket 40 is made from approximately 0.010 to 0.020 inch thick stainless steel. If desired it could also be made of a dental gold alloy or any other generally accepted dental alloys and materials.

Figure 3:
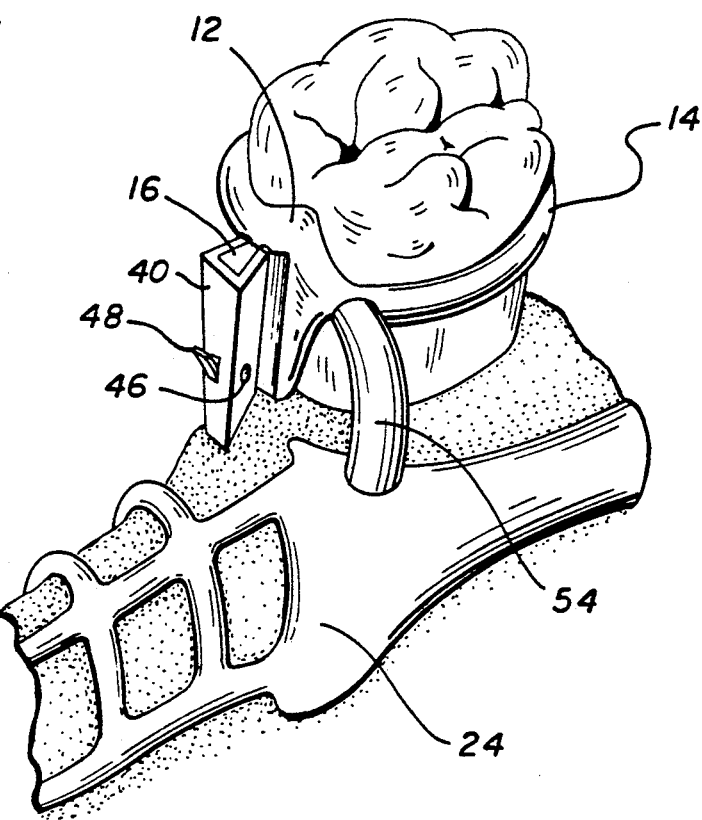
FIG. 3 shows a step in the fabrication of a typical Stress Breaker Appliance ® incorporating the improved female joint portion of this invention.

FIG. 3 shows a step in the fabrication of a typical Stress Breaker Appliance ® 10 incorporating the improved female joint portion 40. At this stage, the forward and rear portions 12, 24 of the Appliance have been cast. The forward portion 12 includes a pair of encircling clasps or any other conventional retainers 14 and an integral male wedge 16. The two segments 12, 24 are retained in strict relation to each other through the casting process by a temporary stabilizer 54. The improved female wedge portion 40 is shown in place on the male wedge 16. One hole 46, and the flap 48 can clearly be seen.

Following fit check, the dental technician would grind a false tooth to receive the female wedge 40. He would remove the temporary stabilizer 54 when the appliance is completed, prior to inserting the pin 36, not shown on FIG. 3. Upon assembly, the flap 48 will retain the female wedge in the dental plastic, usually pink colored methyl methacrylate, which is applied over the gingival area of the false teeth to simulate gums.

Figure 4:
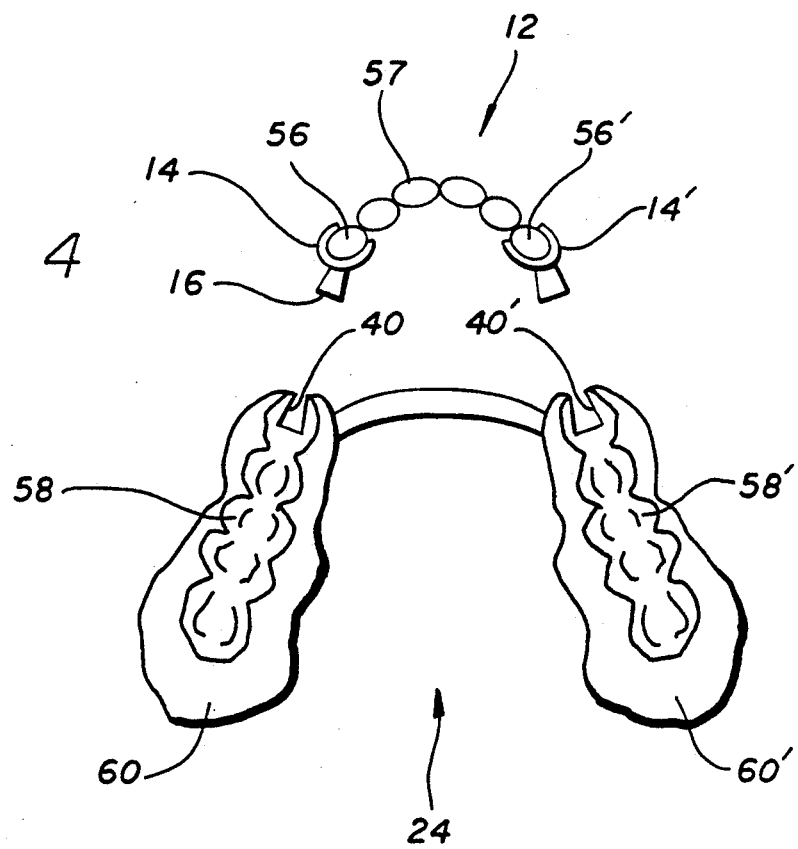
FIG. 4 is an exploded top view of a typical, completed Stress Breaker Appliance ® incorporating the improved female joint portion of this invention.

To clarify this assembly, FIG. 4 shows an exploded, top view of a typical, completed Stress Breaker Appliance ® 10, incorporating the improved female joint portion 40. Here are shown the front portion 12 and the rear portion 24. The front portion, as illustrated, comprises encircling retainers 14, 14', around abutment teeth 56, 56'. Male wedges 16, 16' are attached to the encircling retainers 14, 14'. Other natural teeth 57 are also shown. The rear portion 24 incorporates the female wedge portions 40, 40' embedded in false teeth 58, 58' and dental plastic 60, 60'. In order to clarify construction details, the Stress Breaker Appliance ® 10 is shown in exploded fashion. In actual fact, the two portions 12, 24 would be joined by slipping the wedge portions 16, 16' into the sockets 40, 40'. A pin 36, not shown on FIG. 4, would then be passed through the elongated slot 22 and be retained in the holes 46. Finally, the access holes, again not shown on FIG. 4, in the dental plastic 60, used for inserting the pin 36, would be sealed.

After final assembly, the wedges 16 and 40 can slide against each other but are designed to constrain movement. Because of the respective tapers, the bottom 20 of the male portion 16 cannot pass below the bottom or gingival opening 52 of the female 40. Or looked at from the other perspective, the top or occlusal opening 50 of the female portion 40 cannot pass above the top 18 of the male portion 16. The pin 36 limits the distance that the two members 16, 40 can separate from each other. This allows the two portions 12, 24 of the Appliance to move in relation to each other. The motion is slight and is constrained to an up and down direction as shown by the arrow 38 on FIG. 1. This motion relieves the stresses, induced by chewing, on the abutment teeth 56.

The advantages conferred by use of this improved female member 40 are numerous. First, the improved female member 40 can be made by inexpensive metal forming techniques. Second, using a preformed, female member saves the dental technician's time. Third, the need for repairing casting defects associated with investment casting of the rear portion 24 of the Appliance 10 are vastly minimized. Fourth, the improved female member 40 does not have to be joined to the frame 26 of the rear portion 24: instead it can be embedded in a false tooth 58 and dental plastic 60. Fifth, the flap 48 becomes embedded in the dental plastic 60, thus securely locking the improved female member in place. Sixth, since the improved female member 40 is incorporated into a tooth 58 and plastic 24 instead of the frame 26, repairs are much easier to make.

The improved female socket can be used in upper or lower dental prostheses. Although the present invention has been described in detail with reference to particular embodiments, persons possessing ordinary skill in the art to which this invention pertains will appreciate that various other modifications and enhancements may be made without departing from the spirit and scope of the claims that follow.

What is claimed is:

1. An apparatus comprising:
   a wedge shaped female member (40) for slidably receiving a wedge shaped male member (16), said wedge shaped female member having two side walls (42), a rear wall (44), a occlusal opening (50) and a gingival opening (52),
   said wedge shaped female member (40) tapering in a direction opposite to that of a patient's teeth,
   said occlusal opening (50) being larger than said gingival opening (52), so that said male member (16) is limited from sliding beyond said gingival opening (52),
   each of said side walls (42) having a hole (46) through it, for retaining a pin (36),
   said rear wall being pierced with a flap (48), so that said wedge shaped female member (40) may be securely retained in a false tooth (58) and dental plastic (60).

2. An apparatus as claimed in claim 1 in which said wedge shaped female member (40) is made from a material selected from the group consisting of stainless steel sheet and gold alloy sheet.

3. An apparatus comprising:
  a) at least one retainer (12) configured to engage and be secured to various abutment teeth (56) in a patient's mouth;
  b) a supporting portion (24) configured for mounting and holding dental plastic (60) and at least one false tooth (58);
  c) a wedge shaped male member (16) on said retainer (12); said wedge shaped male member (16) tapering in a direction opposite to said abutment teeth (56), said wedge shaped male member (16) having an elongated hole (22) through it in a direction transverse to said abutment teeth (56);
  d) a wedge shaped female member (40) for slidably receiving said wedge shaped male member (16), said wedge shaped female member having two side walls (42), a rear wall (44), an occlusal opening (50) and a gingival opening (52),
  said wedge shaped female member (40) tapering in a direction opposite to that of said abutment teeth (56),
  said occlusal opening (50) being larger than said gingival opening (52), so that said male member (16) is limited from sliding beyond said gingival opening (52),
  each of said side walls (42) having a hole (46) through it,
  said rear wall being pierced with a flap (48), so that said wedge shaped female member (40) may be securely retained in a false tooth (58) and dental plastic (60); and
  e) a pin (36) extending through said elongated hole (22) in said wedge shaped male member (16) and retained in said holes (34) in said wedge shaped female member (40), so that said wedge shaped male member (16) is retained within said wedge shaped female member (40) and is constrained in its movement.

4. An apparatus as claimed in claim 3 in which said side walls (42) and said rear wall (44) of said female member are from about 0.010 to about 0.020 inch thick.

5. An apparatus as claimed in claim 3 in which said wedge shaped female member (40) is made from a material selected from the group consisting of stainless steel sheet and gold alloy sheet.

* * * * *